July 4, 1950 F. MEILLAND Plant Pat. 958
ROSE PLANT
Filed April 4, 1949
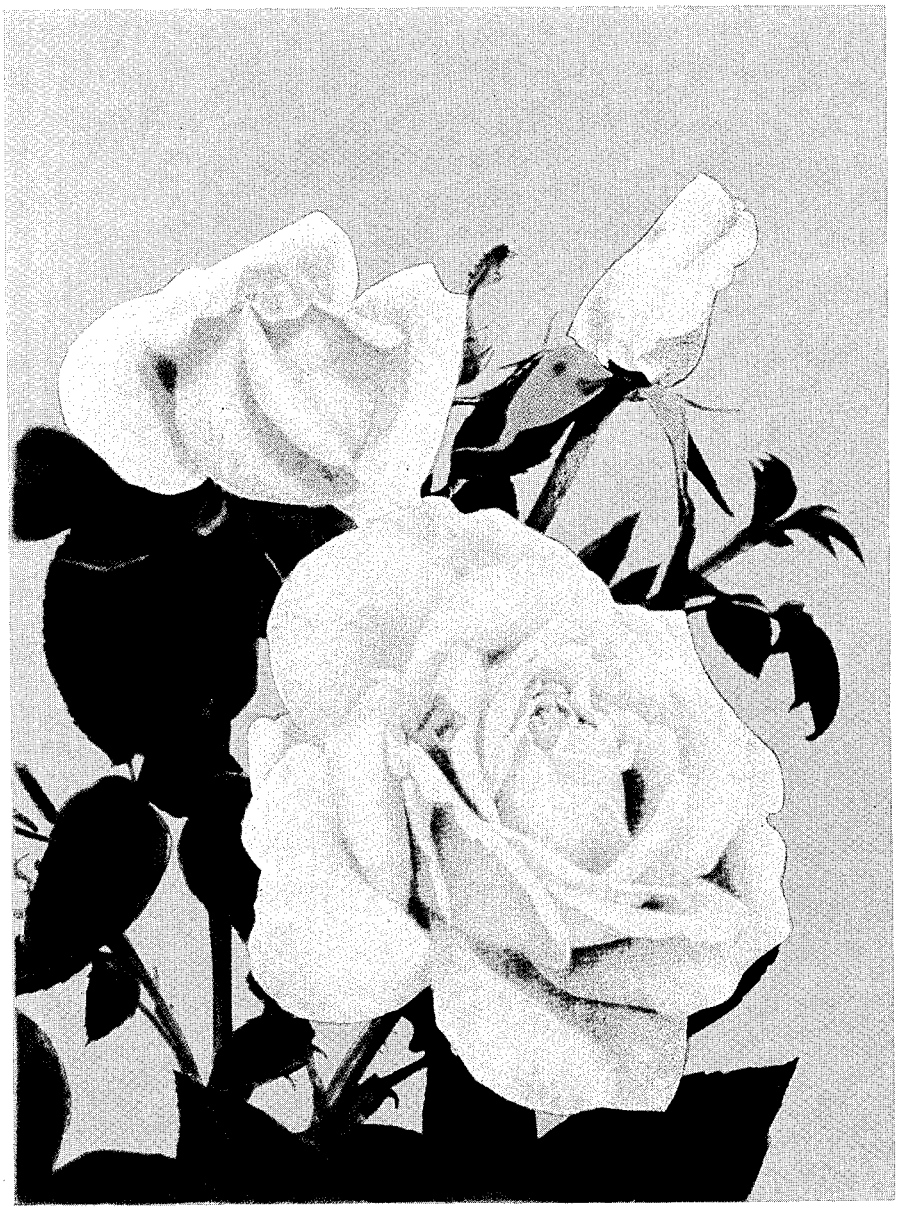
Inventor
F. Meilland
By Robert Robb
By H. C. Robb
Attorneys Patented July 4, 1950

UNITED STATES PATENT OFFICE

958

ROSE PLANT

Francis Meilland, Cap Azura, Cap d'Antibes, France, assignor to The Conard-Pyle Company, West Grove, Pa., a corporation of Pennsylvania Application April 4, 1949, Serial No. 85,397

1 Claim. (Cl. 47—61)

The present invention relates to a new and distinct variety of rose plant constituting a marked improvement over its parents in a number of important respects.

This new variety is characterized by the vigorous growth of the plant, its glossy foliage, its production of unusually abundant blooms of varying pink color tones and of distinctive and superior form, and the large size and strong fragrance of the blooms.

Asexual reproduction of this new variety by budding at Tassin-les-Lyon, Rhone, France, and at West Grove, Pennsylvania, shows the foregoing characteristics come true to form and are established.

The accompanying drawing illustrates specimens of the flowers of this new rose in the various stages of development.

The following is a detailed description of the new variety, all reference to color being in accordance with Ridgway's Color Standards and Nomenclature:

Type: Hardy; bush; outdoor; for cut flowers and garden decoration.
Class: Hybrid tea.
Parentage: Seedling. "Peace" (Pl. Pat. No. 591) × ("Signora," Pl. Pat. No. 201 × "Mrs. John Laing," unpatented).
Propagation: Holds its distinguishing characteristics through succeeding propagations by budding.

*Flower*

Locality where grown: West Grove, Pennsylvania.
Flowers borne: Singly to stem; on strong, medium long stems.
Quantity of bloom: Free; outdoors.
Continuity: Intermittent.
Fragrance: Strong; tea.
Bud:
*Peduncle.*—Medium length; medium heavy; erect; rough; numerous yellow and red prickles (Russet-Vinaceous, Plate XXXIX) at base. Color—Cosse Green, Plate V.
*Before calyx breaks.*—Size—medium large. Form—pointed to globular; with foliaceous appendages on the surface of the bud; with medium stout much-cut foliaceous parts extending beyond the tip of the bud equal to one-fourth or more of its length.
*As calyx breaks.*—Color—Pomegranate Purple, Plate XII, with tinges of Orange-Vinaceous, Plate XXVII.

*As first petal opens.*—Size—medium large. Form—medium long; pointed to ovoid. Color—outside: shading from Empire Yellow, Plate IV, at base to Rose Doree, Plate I, and shading from Nopal Red, Plate I, to Rose Red, Plate XII, at outer edges; occasionally shading from Rose Color, Plate XII, to Tyrian Pink, Plate XII, to Spinel Pink, Plate XXVI, and Light Rosolane Purple, Plate XXVI, at outer edge; inside: shading from Light Cadmium, Plate IV, at base to Strawberry Pink, Plate I, to light Rose Red, Plate XII, and almost to Tyrian Rose, Plate XII, at very apex; occasionally shading from Deep Rose Pink, Plate XII, to Rose Color, Plate XII, at outer edges.
*Opening.*—Opens up well.
Bloom: Size, when fully open—large; 4½ inches to five inches.
*Petalage.*—Double, from 25 to 30 petals arranged regularly.
*Form.*—Very high center at first; remaining high centered; inner petals remaining at first tightly cupped inward with outer row of petals loosely cupped inward; becoming later, at maturity, inner petals loosely cupped inward with outer petals loosely rolled outward.
Petals: Leathery; with inside and outside satiny.
*Shape.*—Outside — round. Intermediate—round. Inside—round.
*Color.*—Colors may be modified by being shaded or washed with other colors.

This description of a newly opened flower was made from a rose grown outdoors in the month of August, at West Grove, Pennsylvania:

*Color.* — *Outside petal* — outside surface: White and Pale Orange Yellow, Plate III, at base, occasionally with a triangular patch of Pomegranate Purple, Plate XII, at base fanning out, and shading to Rose Color, Plate XII, to Spinel Pink, Plate XXVI, and approaching Tyrian Rose, Plate XII, at apex; inside surface: Light Orange Yellow, Plate III, at base shading to Thulite Pink, Plate XXVI, to Rose Color, Plate XII, and Spinel Pink, Plate XXVI, and approaching Tyrian Rose, Plate XII, at outer edge. *Intermediate petal*—outside surface: Pale Orange Yellow, Plate III, at base shading into Spinel Pink, Plate XXVI, underlaid with Pale Orange Yellow, Plate III, and approaching Tyrian Rose, Plate XII, underlaid with Pale Orange Yellow, Plate III, at outer edges, occasionally with a white streak along midrib near apex; inside surface: Empire Yellow, Plate IV, at base shading to Pale Orange Yellow, Plate III, and to Spinel Pink, Plate XXVI, underlaid with Pale Orange Yellow, Plate III. *Inner petal*—Outside surface: shading from Empire Yellow, Plate IV, at base to Pale Orange Yellow, Plate III, to Geranium Pink, Plate I, occasionally with white streaks; inside surface: shading from Empire Yellow, Plate IV, at base to Pale Orange Yellow, Plate III, to Geranium Pink, Plate I, occasionally with streaks of Rose Red, Plate XII.

This description was made from a rose that was open for three days outdoors in the month of August, at West Grove, Pennsylvania:

*Color.* — *Outside petal* — outside surface: White at base, occasionally with a triangular patch of Tyrian Rose, Plate XII, shading to Rose Color, Plate XII, underlaid with white and to Rose Color, Plate XII, at outer edges; inside surface: shading from Buff Yellow, Plate III, and white at base to Spinel Pink, Plate XXVI, underlaid with white to dark Spinel Pink, Plate XXVI, and approaching Tyrian Rose, Plate XII, at outer edge of apex. *Inside petal*—outside surface: Shading from Pale Orange Yellow, Plate III, at base to white to Cameo Pink, Plate XXVI, and to Deep Rose Pink, Plate XII, at outer edge; inside surface: shading from Apricot Yellow, Plate IV, at base to white to Cameo Pink, Plate XXVI, and to Thulite Pink, Plate XXVI, and to Light Rosolane Purple, Plate XXVI, at apex, occasionally with streaks of Spinel Red, Plate XXVI, along midrib.

*General color effect.*—Newly opened flower—Spinel Pink, Plate XXVI. Three days open—shading from Thulite Pink, Plate XXVI, to Spinel Pink, Plate XXVI, and occasionally to Light Rosolane Purple, Plate XXVI, at outer edges.

*Behavior.*—Drop off cleanly.

*Flower longevity.*—Cut roses grown outdoors kept at living-room temperatures—4 to 5 days in August.

*Reproductive organs*

Stamens: Many; arranged regularly about pistils.

Filaments: Medium length; most with anthers. Color—Light Jasper Red, Plate XIII.

Anthers: Medium large; occasionally greatly deformed and fused with petaloids or pistils. Color—Deep Chrome, Plate III, with Pinard Yellow, Plate IV, center stripe.

Pollen: Moderately abundant. Color — Deep Chrome, Plate III.

Pistils: Medium number.

Styles: Uneven; medium length; medium thin; bunched.

Stigma: Color—Empire Yellow, Plate IV.

Ovaries: Some protruding from calyx.

Hips: Short; ovoid; moderately smooth; walls medium thick. Color—Lettuce Green, Plate V.

Sepals: Permanent; moderately long; spear-shaped.

*Plant*

Foliage:

*Leaves.*—Compound of three or five leaflets; abundant; medium size; leathery.

*Leaflets.*—Shape—Oval with apex acute; base round; margin simply serrate.

*Color.*—Mature—

Upper surface—Cedar Green, Plate VI.

Under surface—Asphodel Green, Plate XLI.

Young—

Upper surface—Liver Brown, Plate XIV.

Under surface — Indian Red, Plate XXVII.

*Rachis.*—Medium heavy.

Upper side—Grooved; prickly.

Under side—Moderately prickly, sparsely thorny.

*Stipules.*—Moderately long; medium width; with medium-long points, turning out at an angle of less than 90°.

Disease: Resistant of mildew; moderately susceptible to blackspot.

Growth:

*Habit.*—Upright and branched.

*Growth.*—Vigorous.

*Canes.*—Heavy.

*Main stems.*—Gray-green. *Thorns*—several; medium long; hooked downward; with long narrow base. *Prickles and hairs*—none.

*Branches.*—Color, Asphodel Green, Plate XLI, to Light Cress Green, Plate XXXI. *Thorns*—very few; medium long; hooked downward; with medium narrow base. *Prickles and hairs*—none.

*New shoots.*—Color, Javel Green, Plate V. *Thorns*—few; medium long; hooked downward; with narrow base. *Prickles and hairs*—none.

I claim:

A new and distinct variety of rose plant, characterized as to novelty by its vigorous habit of growth, glossy foliage, prolific blooming habit and richly varied color tones of the bloom, the distinctive and superior form thereof, and the large size and fragrance of the blooms, substantially as shown and described.

FRANCIS MEILLAND.

No references cited.